(12) United States Patent
Qian et al.

(10) Patent No.: US 7,092,094 B2
(45) Date of Patent: Aug. 15, 2006

(54) COORDINATED POLARIZATION FOR SHINY SURFACE MEASUREMENT

(75) Inventors: Xiaoping Qian, Clifton Park, NY (US); Kevin George Harding, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 372 days.

(21) Appl. No.: 10/673,598

(22) Filed: Sep. 29, 2003

(65) Prior Publication Data

US 2005/0068532 A1 Mar. 31, 2005

(51) Int. Cl.
*G01J 4/00* (2006.01)

(52) U.S. Cl. ...................................... 356/369
(58) Field of Classification Search ............... None
See application file for complete search history.

(56) References Cited

U.S. PATENT DOCUMENTS

| 5,625,446 | A | 4/1997 | Bedard | |
|---|---|---|---|---|
| 6,028,671 | A * | 2/2000 | Svetkoff et al. | 356/368 |
| 2002/0089747 | A1 | 7/2002 | Hay | |
| 2003/0112447 | A1 | 6/2003 | Harding et al. | |
| 2003/0137662 | A1* | 7/2003 | Janik et al. | 356/369 |

FOREIGN PATENT DOCUMENTS

| EP | 1 154 247 | 11/2001 |
|---|---|---|
| WO | 97/28429 | 7/1997 |

OTHER PUBLICATIONS

J. Clark et al., Improving Laser Triangulation Sensors Using Polarization, Computer Vision, 1995, Proceedings., Jun. 20, 1995, pp. 981-986, XP010146960, ISBN: 0-8186-7042-8.
Clark, James, et al., "Using Light Polarization in Laser Scanning," Image and Vision Computing, 15:107-117 (1997).
Wallace, A.M., et al., "Improving Depth Image Acquisition Using Polarized Light," International Journal of Computer Vision 32(2):87-109 (1999).

* cited by examiner

*Primary Examiner*—Tu T. Nguyen
(74) *Attorney, Agent, or Firm*—Fletcher Yoder

(57) ABSTRACT

The present disclosure provides for an optical metrology system for scanning an object (106) having a shiny surface. The optical metrology system includes at least one light source (102) configured and adapted to emit a structured light pattern (L) against the surface of the object, at least one first polarizer (108) disposed between the light source and the object such that the light pattern passes therethrough, the first polarizer being configured and adapted to vary at least one of the plane of polarization and the polarization angle of the light pattern, at least one camera (124*a*–124*c*) configured and adapted to take images of the object, and at least one second polarizer disposed between the camera and the object, the second polarizer having a fixed orientation.

24 Claims, 8 Drawing Sheets

COORDINATED POLARIZATION FOR SHINY SURFACE MEASUREMENT

BACKGROUND

The present invention relates to optical metrology systems and methods thereof and, more particularly, to a novel optical metrology system and usage thereof for the coordinated polarization of an illumination beam so that the polarization angle changes simultaneously as the sensor and/or the object to be scanned accomplishes the scan process.

In optical metrology, inter-reflection (i.e., double bounce or secondary reflection) poses a big challenge for surface measurement of shiny objects. Due to specular reflections that can occur among concave surfaces or combinations of surfaces positioned near right angles to each other, the true desired laser lines are often obscured by inter-reflection lines. Such obscuration makes it very difficult to measure shiny surfaces of complex surface geometry without first coating the surface with a highly diffusing material (e.g., a powder and the like) or without first deploying a part specific or laser line specific mask to block light to those regions that produce the secondary and/or specular reflections.

The coating of the surface to be scanned with a highly diffusing material so that there is no inter-reflection or the use of a mask to cover each individual area separately so that there is no inter-reflection adds a step to the scanning/inspection processes resulting in increased costs associated with the inspection process and an inspection process which is slower overall.

Accordingly, the need exists for an improved system and method for the measurement (i.e., scanning, inspecting, etc.) of relatively shiny surfaces.

BRIEF DESCRIPTION OF THE INVENTION

The present disclosure provides for optical metrology systems for scanning an object having a shiny surface. According to one aspect of the present disclosure, an optical metrology system includes at least one light source configured and adapted to emit a structured light pattern against the surface of the object, at least one first polarizer disposed between the light source and the object such that the light pattern passes therethrough, the first polarizer being configured and adapted to vary at least one of the plane of polarization and the polarization angle of the light pattern, at least one camera configured and adapted to take images of the object, and at least one second polarizer disposed between the camera and the object, the second polarizer having a fixed orientation.

According to another aspect of the present disclosure, a method for performing an optical metrology on an object having a shiny surface is provided. The method includes the steps of providing an optical metrology system. The optical metrology system includes at least one light source for emitting a light pattern against the object, at least one first polarizer operatively disposed between the light source and the object, the first polarizers being capable of varying at least one of the plane of polarization and the polarization angle of the light pattern, at least one camera for capturing images of the object, and at least one second polarizer fixedly disposed between the camera and the object. The method further includes the steps of emitting a light pattern, through the first polarizer, against a surface of the object; rotating the first polarizer; and using the camera to capture at least one image of the object, wherein the image is captured through the second polarizer.

BRIEF DESCRIPTION OF THE DRAWINGS

The above features and advantages of the present invention will become apparent from a study of the following detailed description taken in conjunction with the accompanying drawings, in which like reference numerals refer to like elements throughout the several views, and in which.

DETAILED DESCRIPTION OF THE INVENTION

From an analytical standpoint, light may be conceptualized as a particle or as a wave. However, when studying the problems of double reflections and/or inter-reflection, it is useful to consider the wavelike aspects of light. Accordingly, assuming that light travels in a wave, a photon of light, when viewed head-on, travels in a particular plane, i.e., up-and-down, side-to-side, or any angle in between. These particular planes are referred to as "polarization angles". Any group of photons can have a random mix of varying polarization angles. As is known in the art, certain events can cause the polarization angles of photons to align or in the alternative can cause photons having certain polarization angles to be filtered out, for example, with the use of a polarizing lens.

Figure 1:
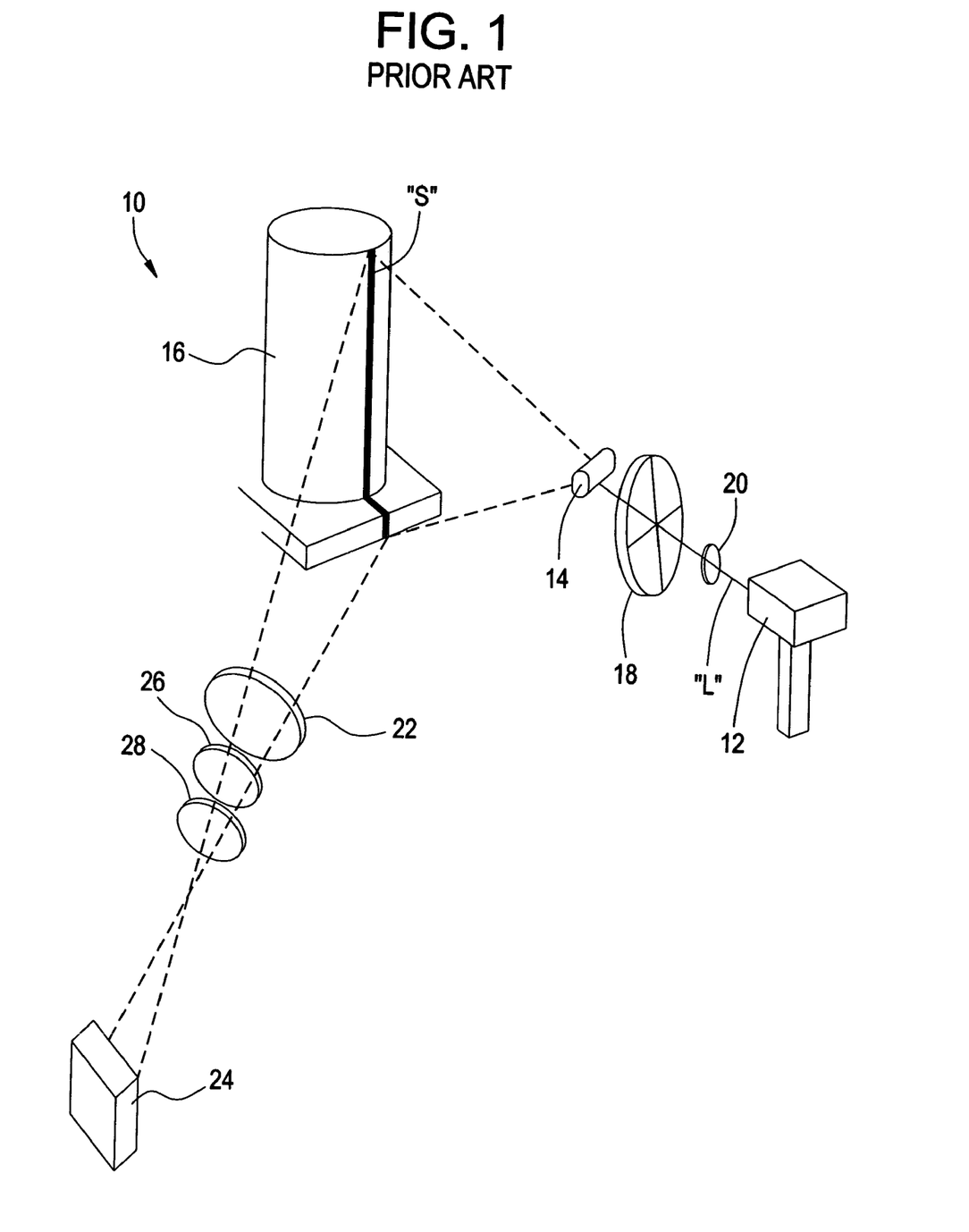
FIG. 1 is a schematic perspective view of an optical metrology system for the scanning of an object, in accordance with the current state of the art.
Figure 2:
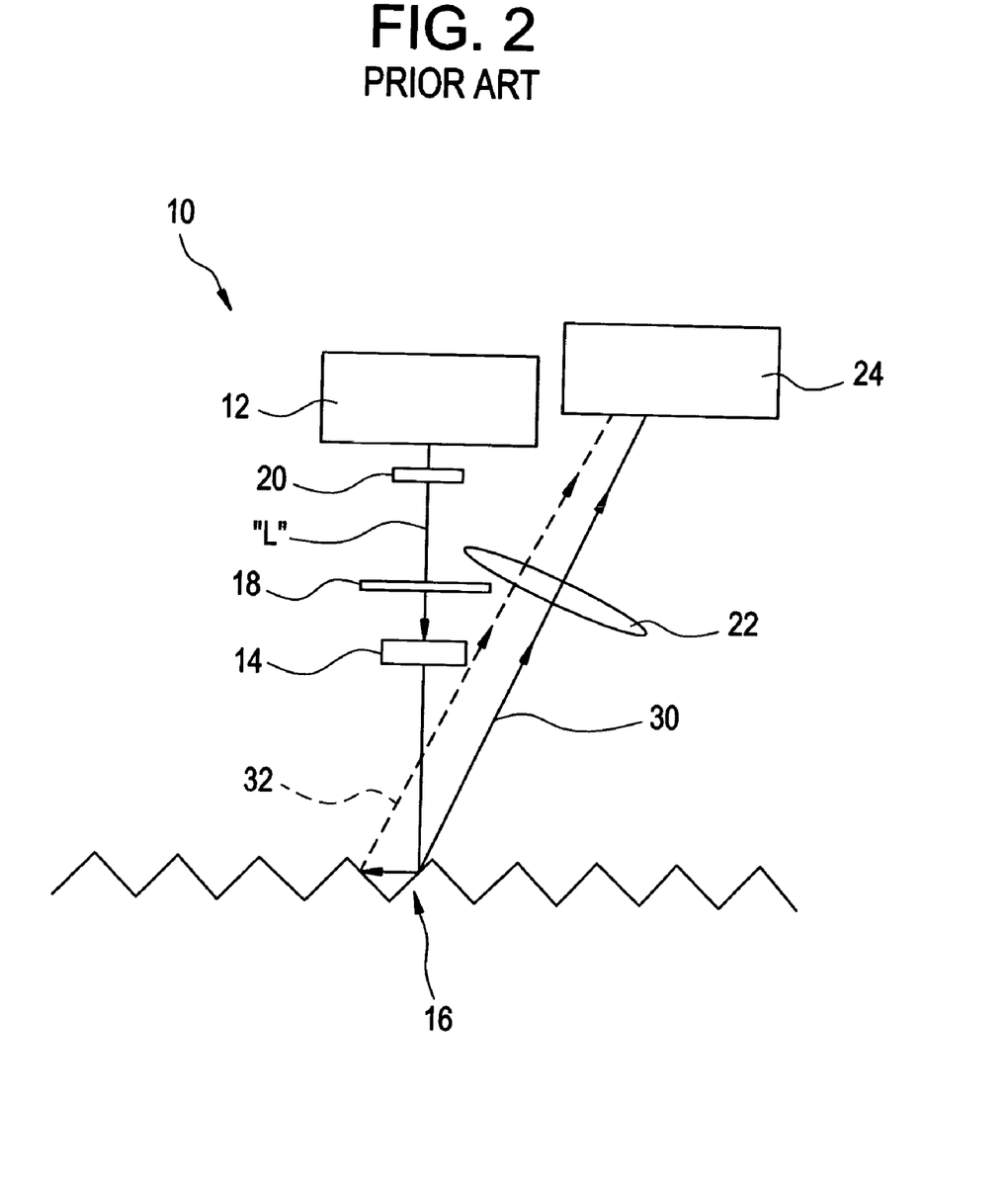
FIG. 2 is a schematic view of the prior art optical metrology system of FIG. 1 illustrating components thereof.
Figure 3:
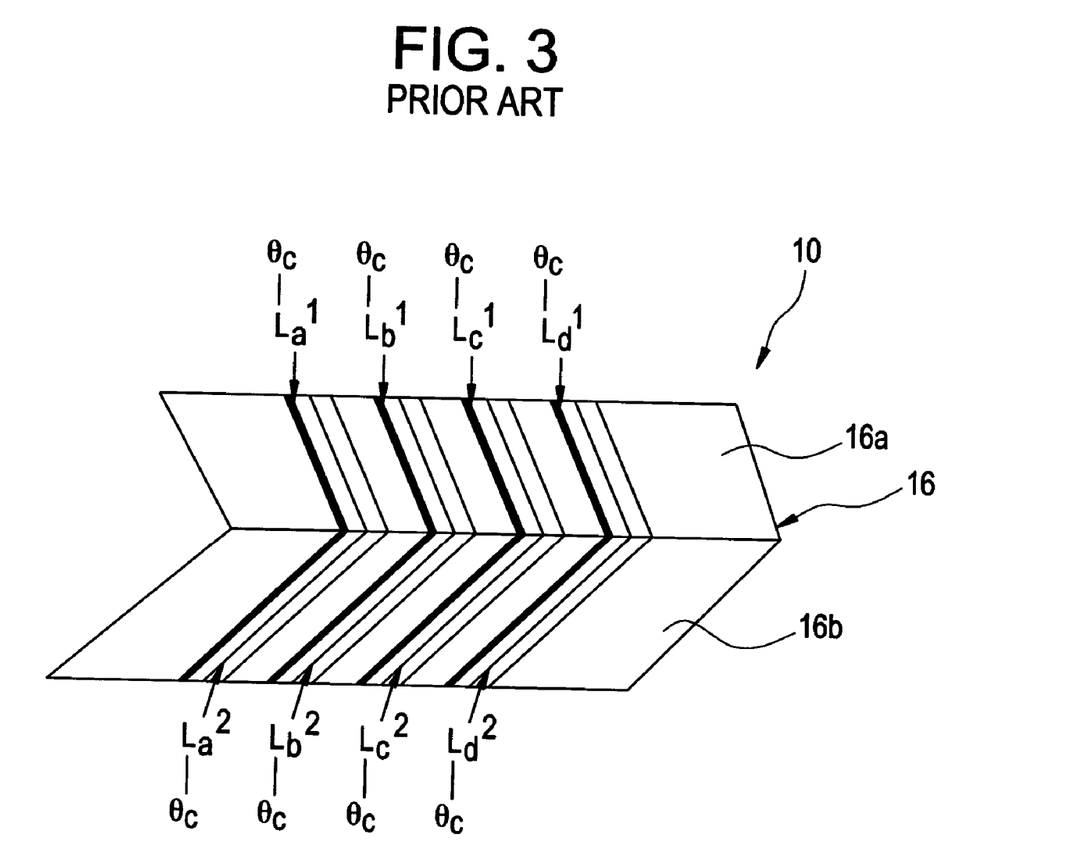
FIG. 3 is a schematic illustration of the optical metrology system of FIGS. 1 and 2.

Referring initially to FIGS. 1–3, an optical metrology system, in accordance with the prior art, for scanning an object having a reflective or shiny surface, is generally designated as 10. As illustrated in FIGS. 1–3, optical metrology system 10 includes at least one laser source 12 (e.g., a diode laser) configured and adapted to transmit at least one laser beam "L" which is collimated and expanded into a stripe "S" by a cylindrical rod lens 14 and then projected onto a surface of an object 16 being observed (e.g., scanned). A first linear polarizer 18 is positioned between collimating optics 20 and rod lens 14 in order to control the plane of polarization and/or a polarization angle. In particular, at least one light source 12, preferably, a laser source, can transmit a first series of structured light patterns (e.g., laser beams) "$L_{a\text{-}d}^{1}$" along one linear stage position and/or reach surface 16a and surface 16b of object 16. The notation "a-d" means that laser source 12 can emit more than one beam at a single time and the notation "1" means that the laser source 12 can emit a first series of laser beams at a first stage position "1"

and/or reach a first surface 16a of object 16. Laser source 12 can also emit a second series of laser beams "$L_{a-d}^2$" which are emitted at a different stage position "2" and/or reach a second or different surface 16b of object 16.

Optical metrology system 10 further includes a second linear polarizer 22 positioned in front of a camera 24. Optical metrology system 10 can further include a neutral density filter 26 for reducing the risk of damage to camera 24 by intense specular reflections of laser source 12. In addition, optical metrology system 10 can further include an infra-red filter 28, fitted to camera 24, to prevent transmission of unwanted wavelengths.

In operation, after each laser beam "L" strikes object 16, each laser beam "L" breaks into a scattered beam 30 and a secondary reflected beam or inter-reflection beam 32 emanating off of object 16. Second linear polarizer 22 is then rotated to one of a number of different angles (i.e., 0°, 45°, 90°, and any angles therebetween) prior to camera 24 acquiring component images. Polarizer 22 is intended to filter out laser beams (e.g., secondary reflected beam or inter-reflection beam) having a polarization angle different than the polarization angle of scatter beam 30. By rotating polarizer 22 to a number of different angles and by taking images at each of the angles to develop an intensity profile for object 16.

In sum, in accordance with the prior art, in use, first linear polarizer 18 is maintained at a fixed polarization angle while second linear polarizer 22 is rotated to a number of different polarization angles such that camera 24 can take a number of images at different orientations of polarizer 22.

Figure 4:
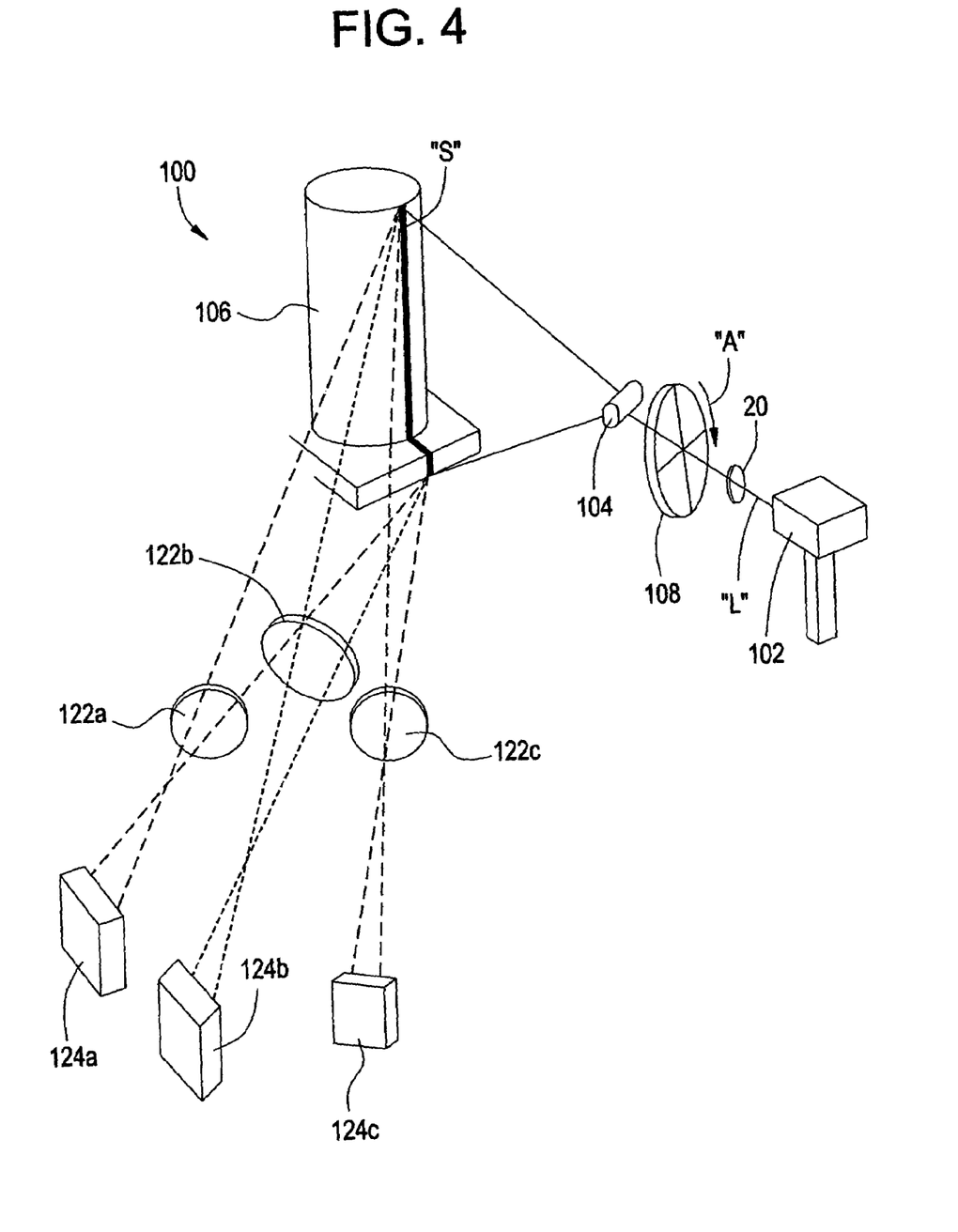
FIG. 4 is a schematic perspective view of an optical metrology system in accordance with an aspect of the present disclosure as it relates to the scanning of an object.
Figure 5:
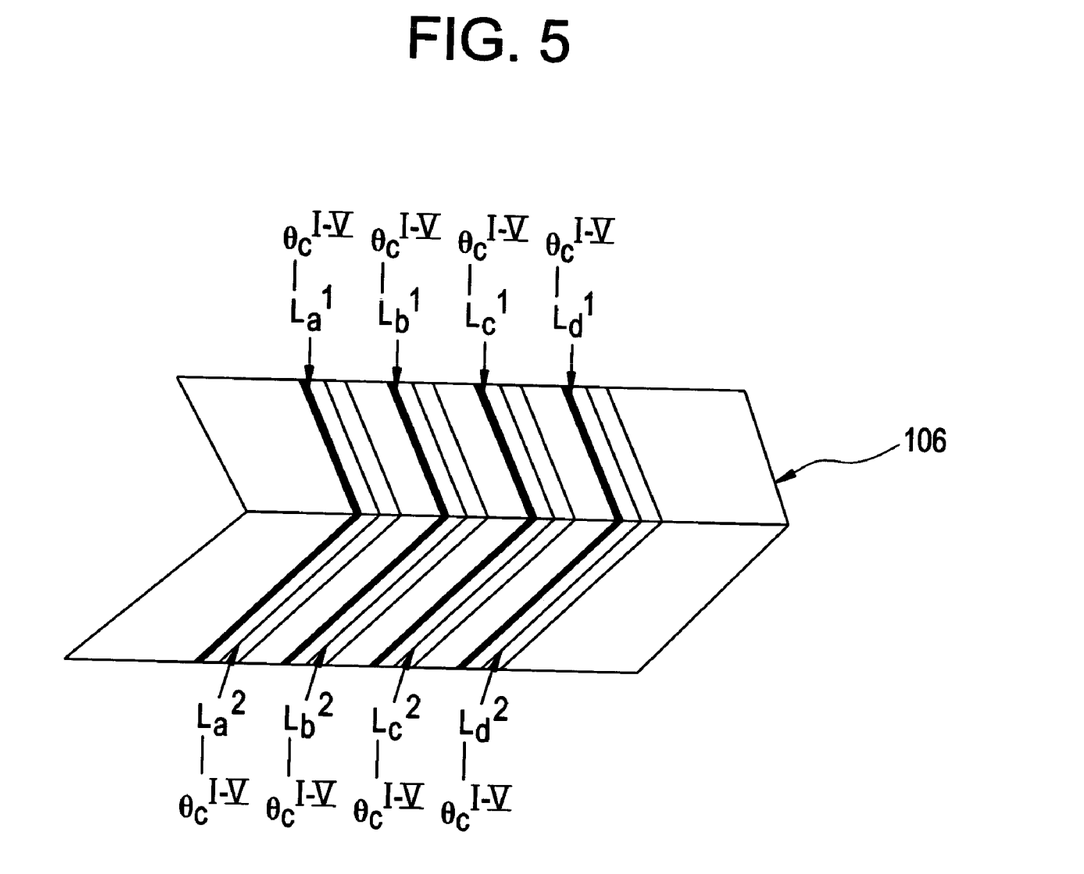
FIG. 5 is a schematic illustration of the optical metrology system of FIG. 4 as it relates to the scanning of an object.

Turning now to FIGS. 4 and 5, an optical metrology system in accordance with an embodiment of the present disclosure is designated generally as 100. As illustrated in FIGS. 3 and 4, optical metrology system 100 includes at least one light source 102, preferably a laser source, configured and adapted to transmit a light pattern "L", preferably a laser beam, which is collimated and expanded into a stripe "S" by a cylindrical rod lens 104 and then projected onto object 106 to be imaged and/or scanned. Optical metrology system 100 includes a first polarizer 108 positioned between laser source 102 and rod lens 104 such that laser beam "L" passes therethrough in order to control the plane of polarization and/or the polarization angle. First polarizer 108 is rotatable, e.g., via a motor-drive rotor (not shown) to vary and change the plane of polarization and/or the polarization angle of laser beam "L". First polarizer 108 is rotatable (as indicated by arrow "A") about an axis defined by laser beam "L". First polarizer 108 includes and is not limited to linear polarizers, circular polarizers and elliptical polarizers. It is envisioned that first polarizer 108 can be driven by phase modulators such as liquid crystals, and electro-optical or photo-elastic modulators which can impose different degrees of phase retardation upon transmission of different degrees of electrical voltage.

Optical metrology system 100 further includes a plurality of camera 124a–124c positioned and oriented to take a plurality of images and/or readings of object 106. While three cameras 124a–124c are shown in FIG. 4, it is envisioned and within the scope of the present disclosure to include any number of cameras (e.g., one, two, four, five, etc.). Each camera 124a–124c includes a corresponding second polarizer 122a–122c positioned between a respective camera 124a–124c and object 106. In particular, each second polarizer 122a–122c is positioned in the line of site and/or the optical field of a respective camera 124a–124c. Each second polarizer 122a–122c is maintained at a fixed angular position and at a different angular position relative to one another. In this manner, each second polarizer 122a–122c filters out (i.e., polarizes) laser beam "L" reflected off of object 106 for specific predetermined polarization angles (e.g., "$\Theta_C^{I\text{-}V}$" of FIG. 5). While three cameras 124a–124c are shown and therefore only three second polarizers 122a–122c having polarization angles "$\Theta_C^{I\text{-}III}$" are needed it is envisioned that at least up to five cameras can be provided for each laser beam and thus five second linear polarizers having polarization angles "$\rightarrow_C^{I\text{-}V}$" are needed. Each second polarizer 122a–122c includes and is not limited to linear polarizers, circular polarizers and elliptical polarizers.

Accordingly, in use, for each laser beam "L" produced by laser source 102 (e.g., "$L_{a-d}$") for each polarization angle of first polarizer 108, cameras 124a–124c take images of and/or scans of object 106 through corresponding second polarizers 122a–122c. Each image taken by cameras 124a–124c includes images of the scattered beam and the inter-reflection beam. The images are then combined to develop an intensity profile for object 106, and to create phase information about and the degree of polarization of object 106. In particular, the images are combined in such a manner so as to amplify the intensity of the scattered beam and to reduce the intensity of the inter-reflection beam.

While cameras 124a–124c are shown positioned on one side of laser source 102, namely, the left hand side as seen in FIG. 4, it is envisioned and within the scope of the present disclosure to position cameras on either side of laser source 102 and/or entirely on the right hand side of laser source 102.

Figure 6:
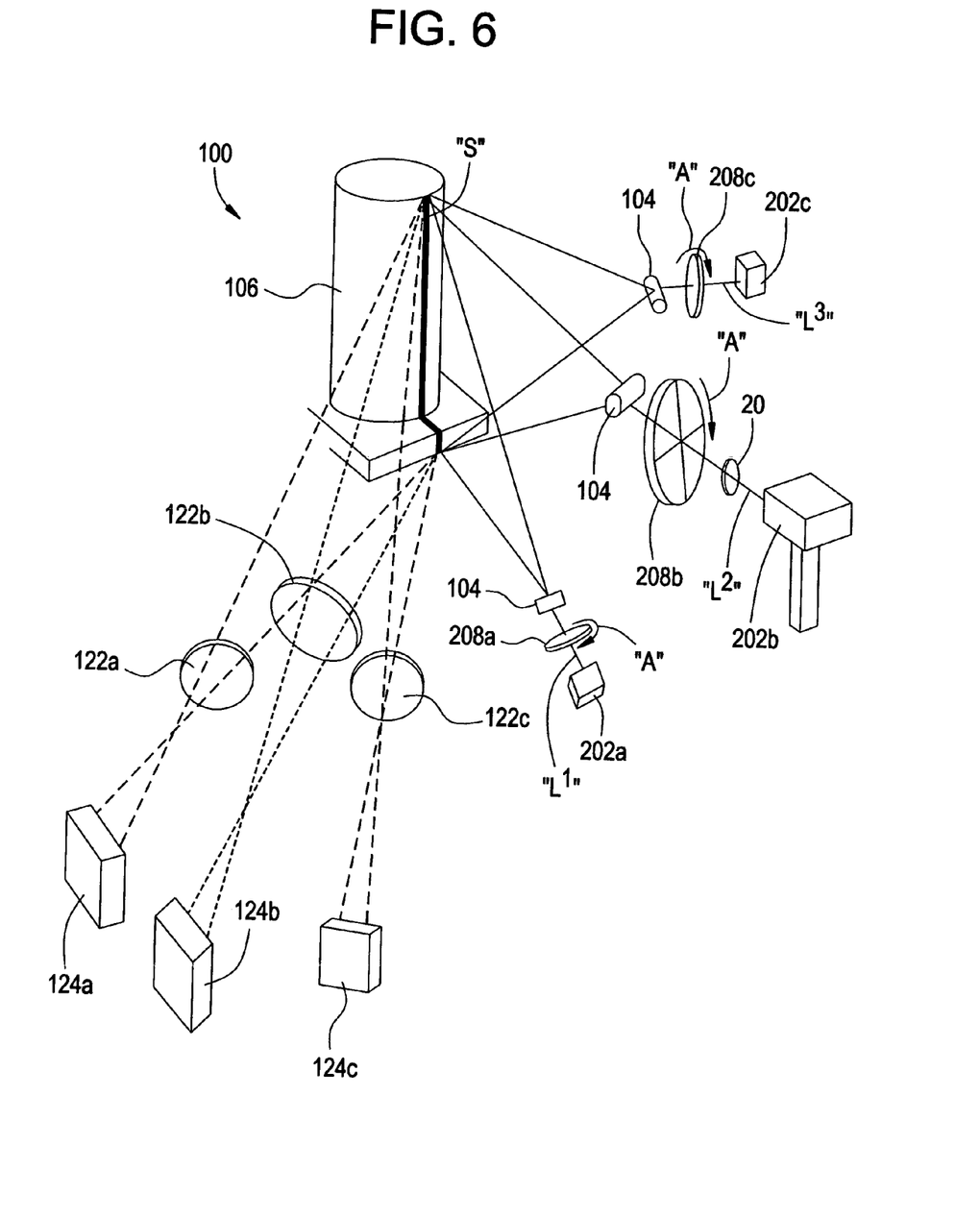
FIG. 6 is a schematic perspective view of an optical metrology system in accordance with another aspect of the present disclosure as it relates to the scanning of an object.
Figure 7:
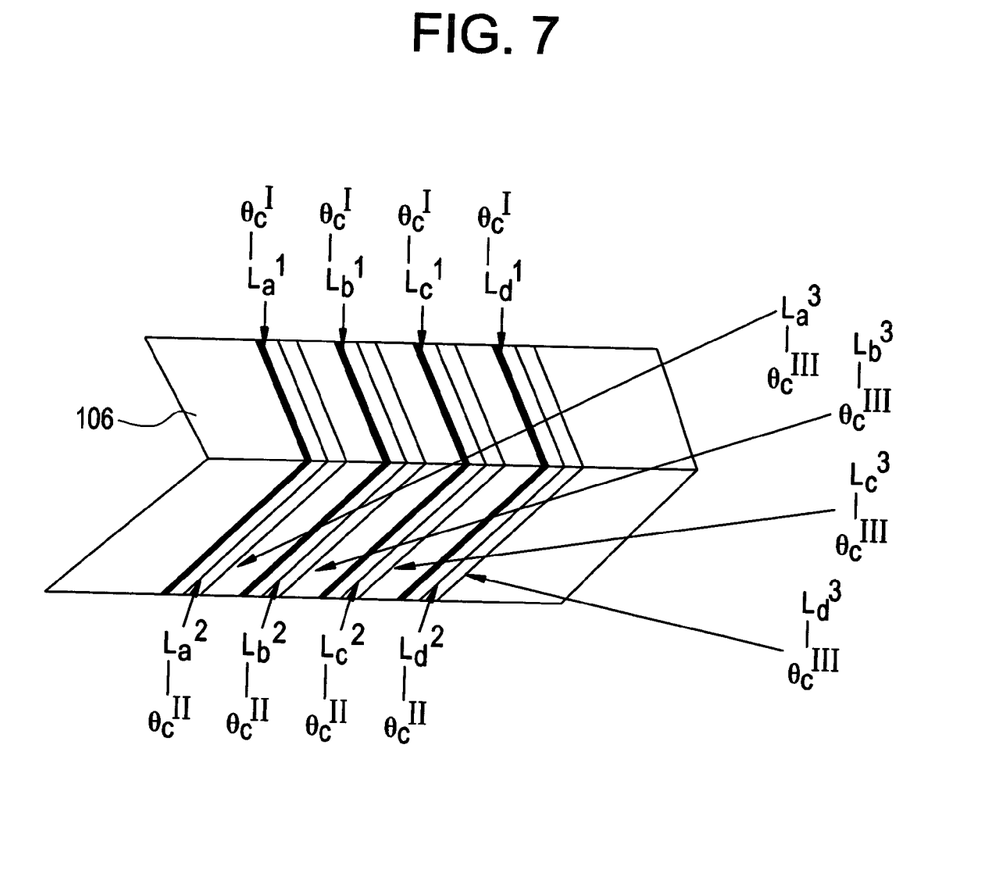
FIG. 7 is a schematic illustration of a optical metrology system in accordance with another aspect of the present disclosure as it relates to the scanning of an object.

With reference to FIGS. 6 and 7, an optical metrology system in accordance with another embodiment of the present disclosure is generally designated as 200. Optical metrology system 200 is similar to optical metrology system 100 and will only be discussed in detail to the extent necessary to identify differences in construction and operation.

Optical metrology system 200 includes a plurality of laser sources 202a–202c each configured and adapted to transmit a respective laser beam "$L^{1\text{-}3}$" against object 106, or, in the alternative, metrology system 200 can include a single laser source configured and adapted to transmit a number of laser beams, e.g., "$L^{1\text{-}3}$", one each, to different positions. Optical metrology system 200 further includes a plurality of first polarizers 208a–208c operatively associated, one each, between respective laser sources 202a–202c and object 106. First polarizers 208a–208c are positioned such that a respective laser beam "$L^{1\text{-}3}$" passes therethrough. Each first linear polarizer 208a–208c is rotatable to vary and change the plane of polarization and/or the polarization angle of respective laser beams "$L^{1\text{-}3}$".

Optical metrology system 200 includes a plurality of cameras 124a–124c each positioned and oriented to take a plurality of images and/or readings of object 106. In particular, as seen in FIG. 6, a camera 124a–124c is provided for a corresponding laser source 202a–202c. Optical metrology system 200 includes a second polarizer 122a–122c positioned between a corresponding camera 124a–124c. Each second polarizer 122a–122c is positioned in the line of sight and/or field of view of a respective camera 124a–124c. Second polarizers 122a–122c are maintained at a fixed angular position and at a different angular position relative to one another, e.g., "$\Theta_C^{I\text{-}III}$" of FIG. 7.

In use, as first polarizers 208a–208c are rotated, each camera 124a, 124c captures at least one image for each corresponding laser beam "$L^{1\text{-}3}$" of laser sources 202a–202c. The images captured by cameras 124a–124c are then combined to develop an intensity profile of object 106, and to create phase information about and the degree of polarization of object 106. It is envisioned that each first polarizer 208a–208c is oriented at a different polarization angle as compared to each other and as compared to an adjacent polarizer 208a–208c.

Figure 8:
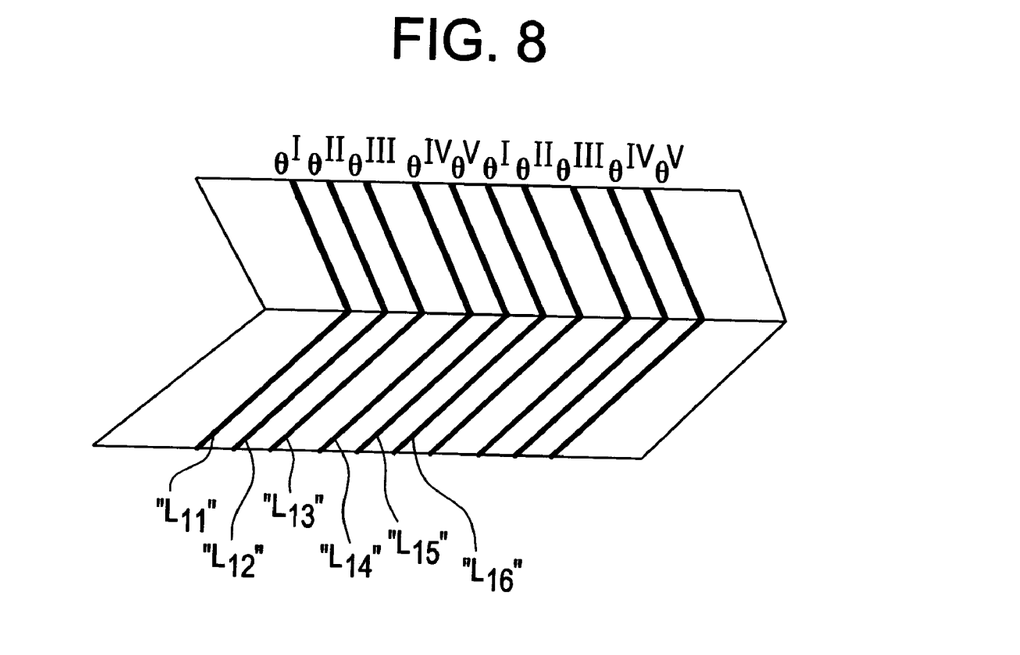
FIGS. 8 and 9 are schematic illustrations depicting the interpolation of phase information during the scanning process.
Figure 9:
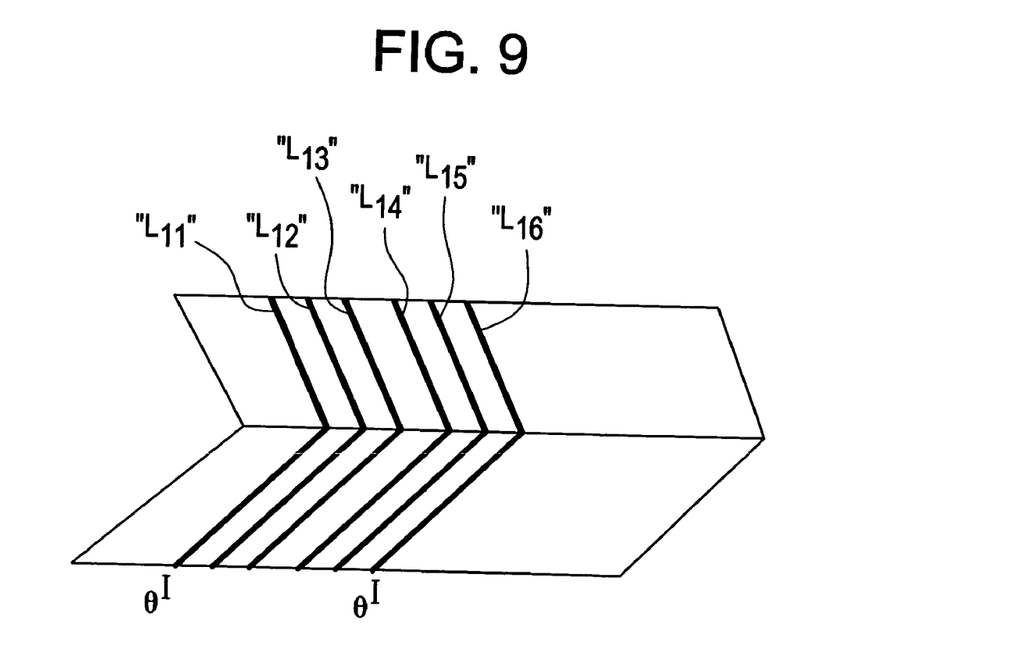

With reference to FIGS. 8 and 9, it is illustrated how the phase information can be interpolated in the image space. In particular, in FIG. 8, at the beginning of the scan process, no phase information is available at a camera polarization angle "$\Theta^j$" corresponding to a first laser beam "$L_{11}$". However, laser beams "$L_{11-16}$" and, in particular, laser beams "$L_{11}$" and "$L_{12}$" are interpolated in order to arrive at an approximate value for the phase information at "$\Theta^j$". Accordingly, as seen in FIG. 9, phase information can be gathered from laser beam "$L_{11}$" at "$\Theta^j$". In particular, the intensity and phase information for a particular location can be determined by capturing a single image for each laser beam "$L_{11-16}$" and then interpolating the information from the captured images.

In view of the above, the optical metrology systems of the present disclosure enable coordinated motion between the angle of polarization of the first polarizers and that of the cameras to provide phase information for each laser beam without reducing the speed of the inspection process. In optical triangular analysis and/or in phase shifting analysis, the coordinated change in the polarization angle of the laser beams emanating from the laser sources combined with the image acquisition by the cameras enables separation of the desired information regarding the object to be scanned from the noise produced by the object to be scanned.

The optical metrology system of the present disclosure also enables the use of multiple cameras having different polarizers with fixed polarization angles in an optical triangular system and/or using multiple cameras in a phase shifting system. It is contemplated that multiple cameras can be provided for taking images of each laser beam.

It is envisioned and within the scope of the present disclosure that either the laser sources can be manipulated to move the laser beam(s) over the object to be scanned or the object to be scanned can be moved relative to the laser beam(s) in order to perform the scan. For example, object 106 can be linearly displaced on a conveyor and the like and/or rotatably displaced on a spindle and the like.

It is further envisioned that the first linear polarizers can be placed on a rotary stage to control the polarization angle thereof. In particular, the polarization can be changed by either providing a single polarizer which can be rotated about a central axis thereof and/or by providing a frame which can be provided which carries a plurality of polarizers thereon and which, when rotated and/or manipulated, positioned a selected polarizer into the path of the laser beam.

It is envisioned that multiple first linear polarizers can be provided for each laser beam and that multiple second linear polarizers can be provided between each camera and the object.

While the preferred forms and embodiments of the invention have been illustrated and described herein, it will be apparent to those of ordinary skill in the art that various changes and modifications may be made without deviating from the inventive concepts and spirit of the invention as set forth above, and it is intended by the appended claims to define all such concepts which come within the full scope and true spirit of the invention.

What is claimed is:

1. An optical metrology system for scanning an object having a shiny surface, comprising:
   at least one light source configured and adapted to emit a structured light pattern against the surface of the object;
   at least one first polarizer disposed between the light source and the object such that the light pattern passes therethrough, the first polarizer being configured and adapted to vary at least one of the plane of polarization and the polarization angle of the light pattern;
   at least one camera configured and adapted to take a plurality of images of the object at different orientations relative to one another; and
   at least one second polarizer disposed between the camera and the object, the second polarizer having a fixed orientation, wherein the system is configured to combine the images.

2. The optical metrology system of claim 1, wherein the light source is a laser source.

3. The optical metrology system of claim 1, wherein the first polarizer is rotatable about an axis defined by the light pattern.

4. The optical metrology system of claim 1, wherein each light source is configured and adapted to emit at least one laser beam against the object.

5. The optical metrology system of claim 1, further including a plurality of cameras configured and adapted to take images of the object at different orientations relative to one another.

6. The optical metrology system of claim 1, wherein each second polarizer is oriented at a different angular position relative to one another.

7. The optical metrology system of claim 1, wherein the first and second polarizer comprises a linear polarizer, a circular polarizer, or an elliptical polarizer, or a combination thereof.

8. The optical metrology system of claim 1, wherein the images at different orientations relative to one another are combined to provide one or more intensity profiles of the object, phase information about the object, a degree of polarization of the object, or a combination thereof.

9. The optical metrology system of claim 1, wherein the system is configured to combine the images to amplify intensity of scattered light and to reduce intensity of inter-reflection light.

10. An optical metrology system for scanning the surface of a shiny object, the optical metrology system comprising:
    at least one light source configured and adapted to emit a structured light pattern against the surface of the object;
    at least one first polarizing lens disposed between the light source and the object, the first polarizing lens being rotatable about an axis defined by the light beam;
    at least one camera oriented to take a plurality of images of the object at different orientations relative to one another; and
    at least one second polarization lens disposed between each camera and the object, each second polarization lens having a fixed orientation relative to one another and having a different orientation relative to one another, wherein the system is configured to combine the images.

11. The optical metrology system of claim 10, wherein the light source is a laser source.

12. The optical metrology system of claim 10, wherein the first polarizer is rotatable about an axis defined by the light pattern.

13. The optical metrology system of claim 10, wherein each light source is configured and adapted to emit at least one laser beam against the object.

14. The optical metrology system of claim 10, further including a plurality of cameras configured and adapted to take images of the object at different orientations relative to one another.

15. The optical metrology system of claim 10, wherein each second polarizer is oriented at a different angular position relative to one another.

16. The optical metrology system of claim 10, wherein the first and second polarizer comprises a linear polarizer, a circular polarizer, or an elliptical polarizer, or a combination thereof.

17. The optical metro logy system of claim 10, wherein the images at different orientations relative to one another are combined to provide one or more intensity profiles of the object, phase information about the object, or a degree of polarization of the object, or a combination thereof.

18. The optical metrology system of claim 10, wherein the system is configured to combine the images to amplify intensity of scattered light and to reduce intensity of inter-reflection light.

19. A method for performing an optical metrology on an object having a shiny surface, the method comprising the steps of:
providing an optical metrology system including:
at least one light source for emitting a light pattern against the object;
at least one first polarizer operatively disposed between the light source and the object, the first polarizers being capable of varying at least one of the plane of polarization and the polarization angle of the light pattern;
at least one camera for capturing a plurality of images of the object at different orientations relative to one another; and
at least one second polarizer fixedly disposed between the camera and the object;
emitting a light pattern, through the first polarizer, against a surface of the object;
rotating the first polarizer;
using the camera to capture at least one image of the object, wherein the image is captured through the second polarizer; and
combining the plurality of images.

20. The method according to claim 19, wherein the system includes a plurality of cameras, and wherein the method includes the step of using each camera to capture the plurality of images of the object.

21. The method according to claim 19, wherein the step of combining comprises combining the plurality of images to separate desired information regarding the object from noise produced by the surface of the object.

22. The method according to claim 19, further comprising the step of interpolating laser beams in the image space to arrive at phase information.

23. The method according to claim 19, wherein each of the first and second polarizers comprises a linear polarizer, a circular polarizer, and an elliptical polarizer.

24. The method according to claim 19, wherein the step of combining comprises combining the plurality of images to amplify intensity of scattered light and to reduce intensity of inter-reflection light.

* * * * *